US009372159B2

(12) United States Patent
Zavodny

(10) Patent No.: US 9,372,159 B2
(45) Date of Patent: Jun. 21, 2016

(54) SYSTEM AND METHOD FOR DETECTING HELIOSTAT FAILURES USING ARTIFICIAL LIGHT SOURCES

(71) Applicant: eSolar Inc., Burbank, CA (US)

(72) Inventor: Maximilian Zavodny, Pasadena, CA (US)

(73) Assignee: eSolar, Inc., Burbank, CA (US)

( * ) Notice: Subject to any disclaimer, the term of this patent is extended or adjusted under 35 U.S.C. 154(b) by 0 days.

(21) Appl. No.: 14/850,916

(22) Filed: Sep. 10, 2015

(65) Prior Publication Data

US 2016/0069817 A1    Mar. 10, 2016

Related U.S. Application Data

(60) Provisional application No. 62/048,783, filed on Sep. 10, 2014.

(51) Int. Cl.
*G01N 21/88* (2006.01)
*G01N 21/55* (2014.01)

(52) U.S. Cl.
CPC ............ *G01N 21/8851* (2013.01); *G01N 21/55* (2013.01); *G01N 2021/8887* (2013.01); *G01N 2201/062* (2013.01)

(58) Field of Classification Search
USPC ............. 356/445; 126/425, 600, 601, 641.15, 126/685; 348/139; 250/203.4, 203.1, 250/559.07, 559.08
See application file for complete search history.

(56) References Cited

U.S. PATENT DOCUMENTS

| | | | | |
|---|---|---|---|---|
| 4,564,275 A | * | 1/1986 | Stone | F24J 2/38 126/602 |
| 5,862,799 A | * | 1/1999 | Yogev | F24J 2/10 126/578 |
| 7,994,459 B2 | | 8/2011 | Zavodny et al. | |
| 8,104,893 B2 | | 1/2012 | Reznik et al. | |
| 8,192,027 B2 | | 6/2012 | Reznik et al. | |
| 8,664,577 B1 | * | 3/2014 | Ghanbari | G01J 1/0411 250/203.4 |
| 2004/0086021 A1 | * | 5/2004 | Litwin | F24J 2/07 374/120 |
| 2005/0274376 A1 | * | 12/2005 | Litwin | F24J 2/10 126/685 |
| 2008/0236568 A1 | * | 10/2008 | Hickerson | F24J 2/38 126/578 |
| 2010/0191378 A1 | * | 7/2010 | Gilon | F24J 2/38 700/275 |

(Continued)

OTHER PUBLICATIONS

Maximilian Zavodny et al., "Tower-based CCP artificial light calibration system", Energy Procedia, May 2015, Pages, vol. 69, Elsevier Ltd., United States.

*Primary Examiner* — Sang Nguyen
(74) *Attorney, Agent, or Firm* — Peter Haderlein

(57) ABSTRACT

A system and method for detecting heliostat failures in a concentrating solar plant, the system comprising a plurality of stationary lights and cameras mounted to towers that surround, or are situated within, a field of heliostats. Heliostats may be commanded via a control system to move to a position wherein light may be expected to be reflected from a given stationary light to a given camera, whereupon a first set of images of the heliostat are taken. Heliostats may then be commanded via the control system to move to a position wherein light may no longer be expected to be reflected from said stationary light to said camera, whereupon a second set of images of the heliostat are taken. An image processor may search the first and second set of images to determine if reflected light is present. If reflected light from said stationary light is not found in the images, the heliostat may be determined to have experienced a failure mode. Failed heliostats may then be flagged for inspection, repair, or replacement.

12 Claims, 6 Drawing Sheets

(56) References Cited

U.S. PATENT DOCUMENTS

| | | | |
|---|---|---|---|
| 2010/0206294 A1* | 8/2010 | Blair | F24J 2/461 126/600 |
| 2011/0000478 A1* | 1/2011 | Reznik | F24J 2/16 126/574 |
| 2012/0174909 A1* | 7/2012 | Koningstein | F24J 2/07 126/601 |
| 2012/0192917 A1* | 8/2012 | Whitted | H02S 20/00 136/246 |
| 2013/0021471 A1* | 1/2013 | Waterhouse | F24J 2/38 348/139 |

* cited by examiner

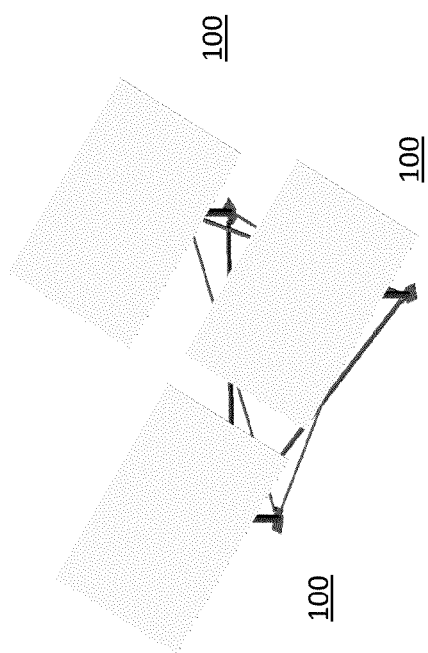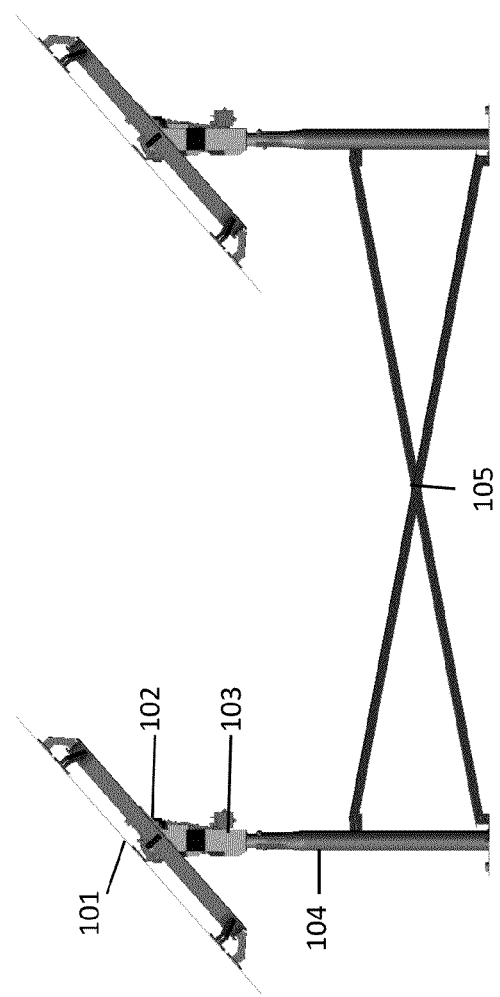

SYSTEM AND METHOD FOR DETECTING HELIOSTAT FAILURES USING ARTIFICIAL LIGHT SOURCES

CROSS-REFERENCES TO RELATED APPLICATIONS

The present application claims priority to and the benefit of U.S. Provisional Patent Application No. 62/048,783, filed on Sep. 10, 2014, the entire disclosure of which is incorporated herein by reference.

BACKGROUND OF THE INVENTION

This disclosure relates generally to a system and method for detecting failed heliostats in a concentrating solar field. In particular, the invention relates to an improved system and method for assessing heliostat operability by reflecting artificial light from heliostats onto camera imagers.

In Concentrating Solar Power (CSP) plants an array of heliostats reflect sunlight toward a receiver mounted atop a tower and containing a working fluid. The working fluid may be, for example, water or molten salts. One type of receiver transfers incident radiant energy to the working fluid to produce high-pressure, high-temperature steam, which may later be fed to a turbine for electrical power generation. Heliostats are generally mounted on the ground in an area facing or surrounding the tower. Each heliostat has a reflector: a rigid reflective surface such as a mirror that tracks the sun through the actuation of a heliostat drive mechanism about at least one axis. Sun-tracking involves orienting the reflector throughout the day so as to optimally redirect sunlight from the sun toward the receiver and maintain the desired temperature of the working fluid. The orientation of each heliostat may be changed by actuating at least one motor to a set position.

The power output of a CSP plant depends directly on the accuracy with which heliostats may reflect light onto a desired region of the receiver tower, as well as the reliability with which heliostats may be actuated to deliver flux; these metrics are known as the heliostat pointing accuracy and heliostat availability, respectively. In particular, heliostat availability may be defined as the fraction of heliostats which are able to deliver flux to their intended target on command at a given time. If a heliostat malfunctions or is otherwise out of service, it is unable to reliably reflect sunlight onto the receiver and so decrements the average availability of the field. The effect of a failed heliostat on the availability is determined according to the following formula:

$$A = 1 - \frac{MTTR}{MTTR + MTBF},$$

where A is the average availability, MTTR is the mean time to repair a failed heliostat, and MTBF is the mean time between failures. The MTTR may be calculated as the sum of the mean time to detect that a heliostat is broken and the mean time to repair or replace it. Because faulty heliostats will continue to lie dormant or point flux at the wrong target until they are replaced or recalibrated, it is desirable to provide a means for detecting heliostat failures as quickly as possible.

Some causes of heliostat failures may be readily identified by electrical diagnostics. These may include complications such as motor malfunctions, short circuits, blown fuses, or improper wiring. The heliostats may be periodically queried for status updates, and heliostats which do not respond after a predetermined interval may be flagged for investigation. It is far harder to detect heliostats which remain capable of actuation and communication, but are no longer capable of delivering flux to the receiver accurately and on demand. This scenario may occur if a heliostat has a broken mirror, has experienced a mechanical failure such as a loose bearing or bolt, or has been disturbed by either personnel, field equipment, or environmental forces (such as wind).

Conventional techniques for monitoring heliostat operability typically include regularly scheduled tests in which each heliostat in the field is directed to reflect sunlight onto a target. If the heliostat is commanded to reflect light onto the target and is unable to do so in a satisfactory manner it may be flagged for further inspection and possible maintenance or repair. The shortcomings of this approach are that it may take a very long amount of time to test every heliostat in an entire field, and any heliostats that are undergoing routine pointing to a target rather than the receiver are unavailable for power production. An additional mechanism for determining heliostat field availability is to monitor the flux delivered from the heliostat field or a subsection thereof and look for a drop in power production from expected levels. This method may prove to be ineffective due to the dependency of flux delivery on a variety of factors including, but not limited to, cloud cover, natural variations in direct normal solar insolation (DNI), and reflector cleanliness. Passive monitoring of plant characteristics like flux delivery and receiver temperature do not assist in identifying which heliostats amongst possibly thousands are to blame, requiring additional time and costs for subsequent focused investigations. Accordingly, there is a need for a method of detecting failed heliostats that is reliable, swift, and does not negatively impact heliostat availability for power production.

SUMMARY OF THE INVENTION

An improved failure detection method is described herein, wherein the method comprises steps for assessing heliostat operability via spot-check tests, logging failure events, and reporting said failure events in order to facilitate rapid replacement and restoration. The present invention utilizes a detection system comprising one or more stationary light sources, one or more cameras, and a control system, wherein the control system functions to operate the cameras and lights during the spot-check tests and may be connected to a network. The stationary cameras may be digital video cameras that may be connected to said network. The light sources and cameras are situated in or near a heliostat field and may be elevated above the heliostats by being mounted, for example, on towers at a predetermined height. Utilizing a plurality of cameras allows for a higher degree of parallel data collection, as multiple heliostats from different sections of the field may be viewed simultaneously. The towers upon which the cameras and lights are mounted may include, for example, the receiver tower or separate camera towers. The light sources may be spaced apart from the cameras on different towers or may be co-located with the cameras on the same towers.

The failure detection system comprises the following components: a control system, wherein the control system may issue commands to the heliostat motors to induce or remove reflection of a given light onto a camera; an image processor, wherein the image processor may process images taken by the cameras and may determine whether reflected light is present in an image of a heliostat; a database, wherein the database may store results of the spot-check tests and diagnostic information about the heliostats and the control system; a notification system, wherein the notification system may process and may disseminate the results from the spot-check tests to a software application or to a user; and a power and communication distribution system, wherein the power and communication distribution system may supply power to the light sources and cameras and may facilitate communication between the components of the control system and the heliostats.

Spot-check tests involve commanding a heliostat-under-test to actuate to a particular set of motor positions such that it reflects a given stationary light onto a given camera. As part of the commissioning process, new heliostats are calibrated to obtain the parameters of corresponding characterization functions. Heliostats may also be routinely re-calibrated during plant operation. Calibrating a heliostat may involve actuating it to reflect light onto a known position and applying a correction factor to its controlling parameters if it fails to accurately position itself. The orientation and position of each heliostat may be predicted from these characterization functions using input motor positions and measurable environmental conditions according to the following:

$$\vec{S} = K(M_1, M_2, \ldots, M_i, E_1, E_2, \ldots, E_j) + \vec{\delta}.$$

Here, $\vec{S}$ is the state vector of a heliostat, which represents the position and orientation of its reflector. It is determined by a function (K) of the control inputs ($M_i$) and other environmental conditions ($E_j$), to within some tolerance ($\vec{\delta}$). Environmental conditions may comprise variable forcing effects such as wind or installation and manufacturing tolerances. In such a system with stationary lights and cameras, a set of motor positions may be found that produces a reflection of a certain light into a certain camera. Aside from the effect of environmental conditions, which are typically small compared to the effect of control inputs, this set of motor positions is also stationary in time. During a spot-check test, one or more points are selected in input parameter space, which is the space spanned by motion of the reflector in at least one axial direction. The at least one axial direction may comprise an azimuth axis and an elevation axis. The axes may be orthogonal to each other or may be oblique. The points are defined by the drive motor positions that produce the desired heliostat orientation and position.

The points comprise two types: "bright" points and "dark" points. The bright points may be selected such that the heliostat, if positioned at the point, reflects a given light into the imager lens of a given camera. For each of the bright points, a nearby dark point may be selected from the same input parameter space, wherein each dark point may be selected such that the heliostat, if positioned at the point, will not reflect light into the camera. The bright and dark points may be associated with the heliostat and may be saved to a database. For a given heliostat, a set of points comprising at least one bright point and a set of points comprising at least one dark point may be selected for multiple combinations of cameras and stationary lights. To detect heliostat failures, heliostats may be commanded to move to the bright points, followed by moving to the dark points. If upon moving to the bright points the heliostat successfully reflects light from the given stationary light to the given camera, and if upon moving to the dark points a reflection of the light is not viewable by the camera, the heliostat may be said to have passed the spot-check test and may be considered operable. Alternatively, the pass or failure condition may be defined by the number of bright points which do not produce a reflection of viewable light on the camera and/or the number of dark points that do produce a reflection of viewable light. If a heliostat fails the spot-check test, it may undergo subsequent follow-up testing and diagnostics to determine the nature of the failure mode.

The method for detecting heliostat failures may comprise two phases: a commissioning phase followed by a monitoring phase. The commissioning phase may comprise the following steps:

a) Calibrate a heliostat and define any characterization function parameters.
b) Select said heliostat, a camera, and a stationary light and associate them as a heliostat-camera-light triplet;
c) Test said heliostat's ability to accurately reflect light onto a target via a pointing test. This step may be optional during select instances of the commissioning phase.
d) Simulate the heliostat's expected performance based on the results of the pointing test. This step is optional pending the completion of step (c).
e) For a given heliostat-camera-light triplet, determine two sets of motor positions for each heliostat: one or more that induces a reflection of light from said stationary light onto said camera (a set of "bright points"), and one or more that do not result in said reflection (a set of "dark points").
f) Store said motor positions in a database as a set of bright points and dark points associated with full heliostat operability.

The monitoring phase may comprise the following steps:

a) Select a heliostat from amongst the field.
b) Perform a spot-check test using at least one of the pre-defined sets of motor positions associated with bright and dark points.
c) Store the results of the spot-check test, including relevant diagnostic information, in a database.
d) Process the results of the spot-check test to determine whether a heliostat failure is present.
e) Deliver a notification containing the heliostat's operability status to an automated software application or to users on the network.
f) Adjust the frequency of scheduled spot-check tests and the set of heliostats to be tested according to input from the user or said automated software application.

As set forth in step (e) of the monitoring phase, the detection system may deliver failures to an automated software application or to users on a network. The automated software application may be configured to interface with the control system to automatically perform additional diagnostics, tests, or recalibration of the heliostat as prompted by the results of the spot-check test. The users may comprise maintenance personnel, who may be notified at the conclusion of periodic spot-check tests that heliostats may have failed; these personnel may then troubleshoot units as rapidly as plant economics dictate.

Because the spot-checks may be scheduled to occur at night-time, heliostats may be repaired or recalibrated, and returned to operation while the solar plant is offline. Performing spot-check tests on heliostats is quicker than attempting to recalibrate heliostats, as calibration tests typically require multiple reflections from a greater number of heliostat positions. The method of the present invention improves overall heliostat availability both by lowering the mean time to repair a unit and by not diverting still functional heliostats from power production duty for periodic functional tests. The proposed process of detecting heliostat failures thus provides unique benefits over prior methods.

BRIEF DESCRIPTION OF THE DRAWINGS

FIGS. 1A-1B are isometric and side views, respectively, of example heliostats comprising reflectors mounted to two-axis drive assemblies.

DETAILED DESCRIPTION OF THE PREFERRED EMBODIMENTS

Figure 2:
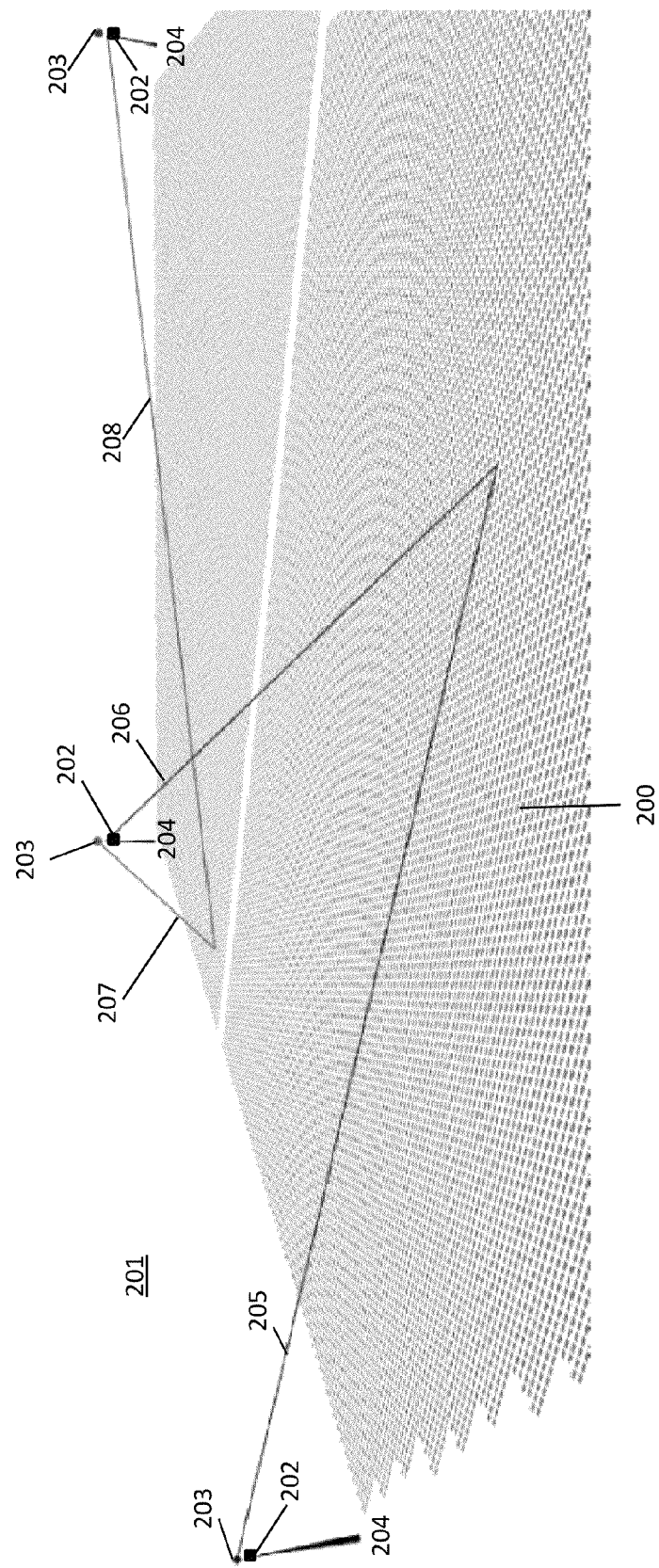
FIG. 2 is a depiction of a failure detection system installed proximate to a heliostat field, wherein the detection system comprises cameras and stationary lights mounted to towers along the field periphery. The figure also depicts the lines of sight from the cameras to sample heliostats in the field.

FIGS. 1A and 1B display examples of heliostats checked by the method of failure detection according to the present invention. FIG. 1A is a perspective view of a group of three heliostats, while FIG. 1B is a side view of the same group. Each heliostat 100 may comprise a reflector module 101 attached to a reflector module channel 102 of drive 103. The reflector module may have a planar shape, such as a flat quadrilateral, or a non-planar shape such as a concave parabolic dish. The reflector module may also comprise a plurality of segmented reflectors arranged in a planar or non-planar shape. The drive 103 may comprise two gear boxes and motors that actuate the drive about two axes. The axes may be in the azimuth (orthogonal to the ground) and elevation (orthogonal to the azimuth axis along the length of the reflector module channel) directions, or they may be linearly actuated axes as, for example, in a Tilt-Tilt configuration. The drive 102 may interface with a post 104 of a heliostat structure assembly 105. Heliostats may further comprise control boards (not shown) internal to the drive that receive power, actuate the motors, and facilitate data communication to and from a network. Actuation commands may be issued to the heliostats over the network from a control system.

FIG. 2 displays a heliostat field 200 and a detection system 201 according to an embodiment of the present invention. The detection system may comprise cameras 202 and stationary lights 203 mounted to towers 204. The towers may comprise dedicated camera towers or a receiver tower (not shown). The stationary lights and the cameras may be co-located on the same towers or distributed amongst different towers. The cameras and the stationary light sources may be mounted to the same holding fixture for interfacing with the towers. Cameras and stationary lights may be positioned throughout the field such that each heliostat may reflect the flux of at least one light to at least one camera, or reflect the flux from a plurality of stationary lights onto a plurality of different cameras. The cameras may be digital imagers capable of capturing both still photographs and video. The stationary lights may be incandescent, fluorescent, or light emitting diodes of a plurality of colors, such as white, red, green or blue. Using lights of different colors on different towers allows for light reflected simultaneously on the same camera from multiple heliostats to be differentiated. This allows for improved parallelism as more heliostats may be checked for operability via spot-check tests using the same camera, reducing the mean time to repair of failed units. Heliostats may be commanded by the control system to reflect light from a given stationary light to a given camera, as depicted by lines of sight 205-208.

Figure 3:
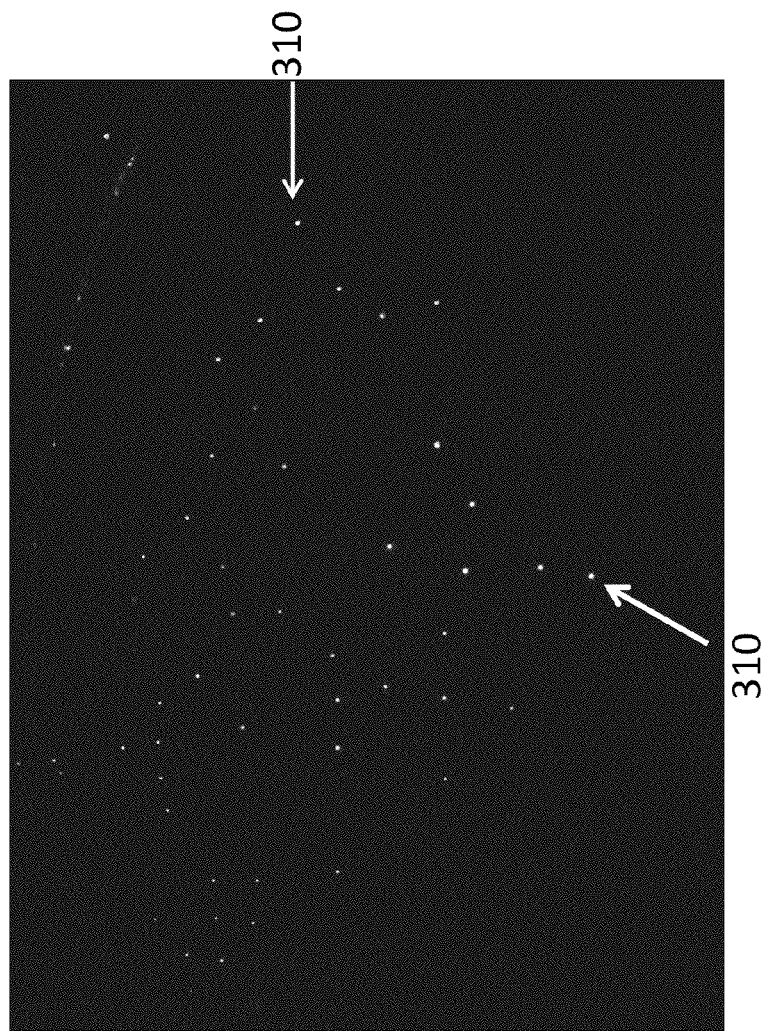
FIG. 3 is an image taken from a tower-mounted camera of a heliostat reflecting light onto the imager.

FIG. 3 displays an example of an image taken by a tower-mounted digital camera. In the image, contiguous regions of brightly colored pixels 310 are visible. These contiguous regions represent light from two stationary light sources reflected onto the camera viewport. They are easily discernible due to the darker surrounding pixels, which appear dark due to the image being taken at night time or through a filter covering the camera lens. The filter may comprise a neutral density filter having a reflective coating. The filter serves to attenuate sunlight reflected from the heliostats onto the camera during the day. The optical density of the filter may be selected such that the camera is not exposed to harmful levels of sunlight during the day while at the same time allowing for reflected light from the stationary light sources to remain visible in pre-processed images.

The following details the process of selecting sets of bright and dark points for a given heliostat. These points may be established during a commissioning phase, after which they may be repeatedly consulted during subsequent spot-check tests. For any combination of heliostat, camera, and stationary light, there is a finite region in the heliostat's motor input parameter space which will induce a reflection of the light source to be seen by the camera. The extent of this region is determined by the geometry of the heliostat-camera-light triplet, as well as the properties of the heliostat surface, such as its curvature profile.

The bright points may be the set of motor inputs that result in the heliostat reflecting light from a given light source into a given camera. The dark points may be the set of motor inputs that result in the heliostat no longer reflecting light from said light source into said camera. Two points that comprise a bright-dark pair may be selected such that they are sufficiently close to each other in input parameter space. Sufficient proximity of the points may be obtained if the transition between points results in a perturbation of at least a predefined size in the kinematic function of the heliostat. For example, the bright and dark points in a pair may be separated by an appropriately small distance from either side of the transition from reflection to non-reflection. This distance may comprise a one milliradian revolution of the reflector about either the azimuth or elevation axis. Bright and dark points may also be selected based on their sensitivity to perturbations of the heliostat in a given axial direction. For example, if the heliostat is considered likely to shift positions when exposed to external forces, such as wind, points may be selected such that reflections from heliostats at the bright and dark points remain distinguishable.

Selecting multiple bright and dark points allows for outlier, erroneous points to be disregarded in favor of more accurate measurements. For instance, multiple bright and dark points may be selected to ensure sufficient sensitivity to perturbations in a given axial direction. A first dark point may be selected to identify a shift in the azimuth direction, and a second dark point may be selected to identify a shift in the elevation direction. Multiple bright points may be selected such that each bright point corresponds to a different position on the reflector surface. This may be done to correct for false negative results, such as when a part of the reflector is blocked or shaded by a neighboring reflector or obstruction, or if a part of the reflector has a convex curvature or is dirty, resulting in a dim, or partially occluded reflection.

Figure 4:
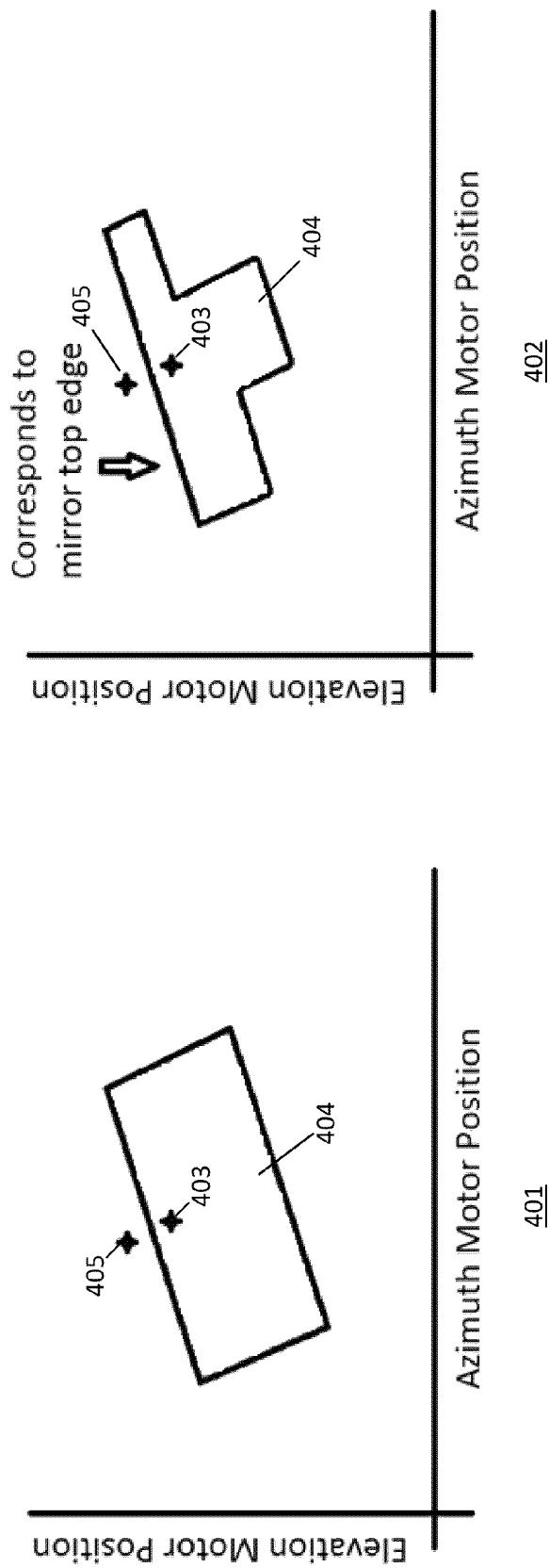
FIG. 4 is a diagram detailing a qualitative representation of the failure detection method using the camera system.

FIG. 4 displays a schematic of where bright and dark points are selected. In heliostat fields of high density, or if the camera or stationary light reside at a particular angle, the line of sight from the heliostat to the light or to the camera may be partially obscured by neighboring heliostats or other items. This blocking and/or shading effect may conflate the results of the spot-check tests if light captured in the camera image is actually reflected from a different heliostat than intended, or if the reflected light is never seen by the camera due to an obstruction. Therefore, neighboring heliostats which may interfere with the reflection may be held in a controlled state during the determination of sets of bright and dark points and subsequent spot-check tests. Additionally, the points in input parameter space may be selected such that light is reflected from part of the heliostat reflector which may never be obscured by neighboring heliostats or other items. This is visible in the comparison of plots 401 and 402 that depict azimuth motor position vs. elevation motor position. An example bright point 403 may be selected from the input parameter space 404 that will produce a reflection of a light into a camera and an example dark point 405 may be selected from the input parameter space that will not produce a reflection of a light onto a camera. In the left plot 401, the input parameter space 404 of a planar heliostat is not obscured by any nearby object, while in the right plot 402 the parameter space is obscured by neighboring heliostats and is reduced in size. The bright point may be chosen such that light will be reflected from a portion of the mirror that is guaranteed to be unaffected by blocking or shading, for example near the top edge of the reflector. The dark point may be chosen such that light will not be reflected from the mirror, for example off the reflector entirely. The bright and dark points may be selected to be in close proximity according to the metric described previously.

If the reflector module has a non-planar shape, the input parameter space may have a variety of different shapes, and it may not be obvious which part of the region in the parameter space corresponds to a region on the surface of a given reflector. In this case the point may be selected using an edge detection method. The edge detection method may comprise obscuring all but the desired portion of the reflector by actuating neighboring heliostats or other objects, and selecting a set of bright and dark points and performing spot-check tests as described previously. Alternatively, the edge detection method may comprise estimating or measuring the reflector to create a mapping from a position on the reflector to a position in input parameter space. This mapping may be used in a simulation to find the point in input parameter space that corresponds to the point on the reflector surface. Creating said map may require the actuation of a plurality of neighboring heliostats to reduce blocking and shading.

Figure 5:
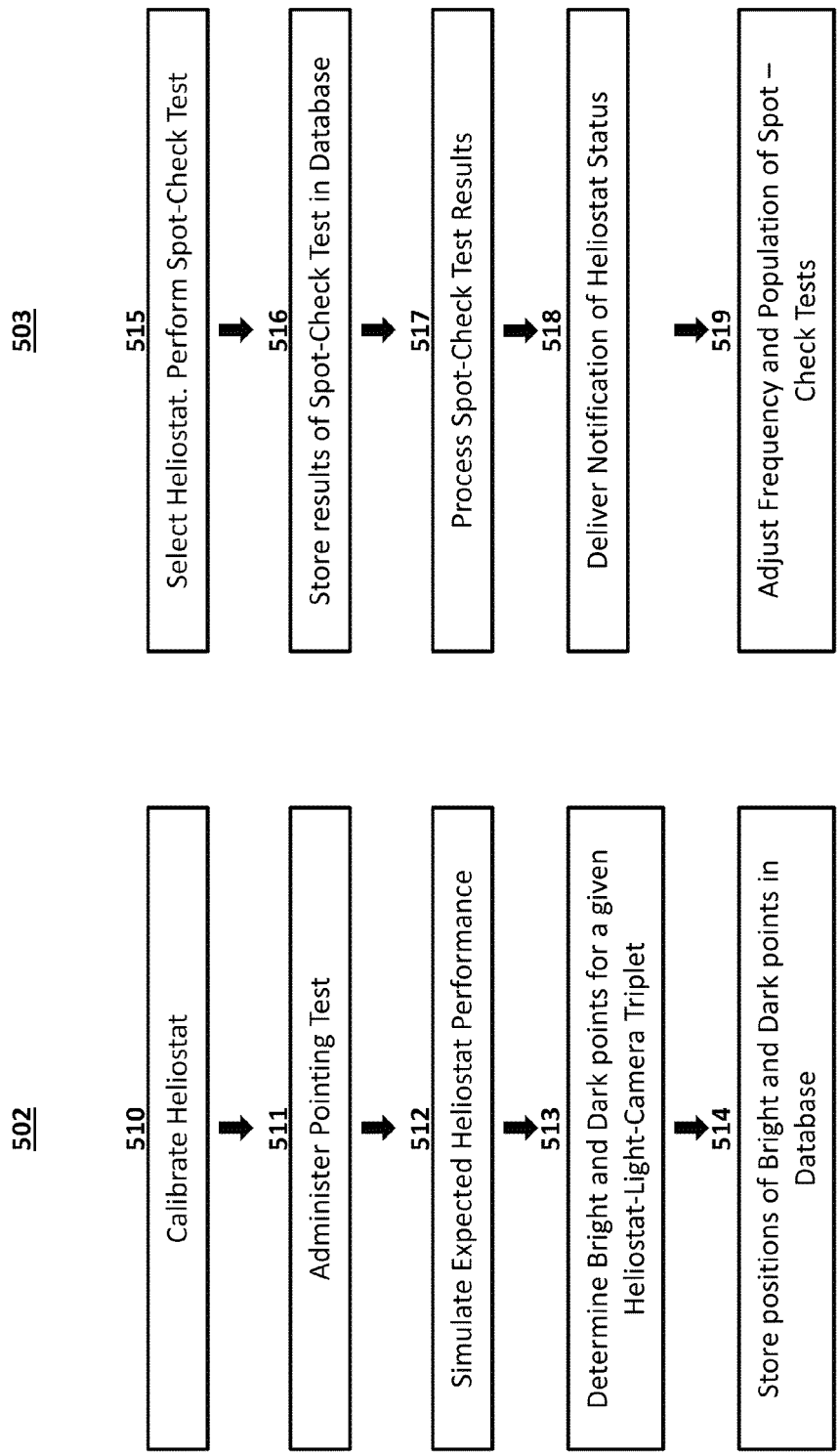
FIG. 5 is a flowchart detailing an embodiment of the method by which failure detection of heliostats is effected using the camera system.

FIG. 5 displays a flowchart 501 detailing the steps of a method of detecting heliostat failures according to a first embodiment of the present invention. The method comprises two phases: a commissioning phase 502 and a monitoring phase 503. The commissioning phase 502 comprises the following steps:

a) Calibrate the heliostat and define characterization function parameters (510). A heliostat may be calibrated by any process that estimates the parameters necessary for it to continuously reflect sunlight onto a receiver tower under open-loop control. For example, a heliostat may be actuated so as to produce a reflection of a given light source in such a way that it is detectable by a given camera, and the control system may record information related to the heliostat's angular orientation at which one or more such reflections were produced, such as the step positions of the motors, as well as the time at which such a reflection occurred, the sun's current position, and other environmental conditions. Characterization function parameters may incorporate input motor positions and measurable environmental conditions according to the following equation: $\vec{S}=K(M_1, M_2, M_i, E_1, E_2, \ldots, E_j)+\vec{\delta}$, where $\vec{S}$ is the state vector of a heliostat determined by a function (K) of the control inputs ($M_i$) and other environmental conditions ($E_j$), to within some tolerance ($\vec{\delta}$).

b) Test the heliostat's ability to accurately reflect light onto a target via a pointing test (511). The pointing test may involve, for example, commanding the heliostat to reflect light onto a target.

c) Simulate the heliostat's expected performance based on the results of the pointing test (512). This step may comprise simulating the flux delivery from a model heliostat having the same pointing accuracy and calculating its contribution to overall plant performance.

d) For a given triplet of a heliostat, stationary light, and camera, determine two sets of motor positions for each heliostat (513), one that induces a reflection of said stationary light onto said camera, and one that removes said reflection. This step involves the selection of bright and dark points for spot-check tests, as previously described.

e) Store said motor positions in the database as a set of bright points and dark points associated with full heliostat operability (514).

The monitoring phase 503 comprises the following steps:

a) Select a heliostat from amongst the field and perform a spot-check test using at least one of the pre-defined sets of bright and dark points (515).

b) Store the results of the spot-check test, including relevant diagnostic information, in the database (516).

c) Process the results of the spot-check test to determine whether a heliostat failure is present (517).

d) Deliver a notification containing the heliostat's operability status to an automated software application or to users on the network (518).

e) Adjust the frequency of scheduled spot-check tests and the set of heliostats to be tested according to user input (519).

Because the positions of the bright and dark points may be repeatedly utilized to ascertain heliostat functionality, it is critical that they correspond to locations having consistently discernible differences in brightness. Therefore, the method of detecting heliostat failures may further comprise the step of testing that the heliostat's pointing accuracy before and after the commissioning phase is at least a given threshold; this may be achieved, for example, by commanding the heliostat to reflect sunlight onto a target screen.

The same stationary lights and cameras that are used for failure detection purposes may also be used to calibrate the heliostats. The step of calibrating a heliostat may comprise mapping its known motor positions to the position of a reflection from said heliostat. The method of detecting heliostat failures may further comprise the step of verifying that the positions of the bright and dark points are consistent with calibration data that relates the motor positions to true heliostat orientation. The locations of the bright and dark points may also be derived from the calibration data itself.

Figure 6:
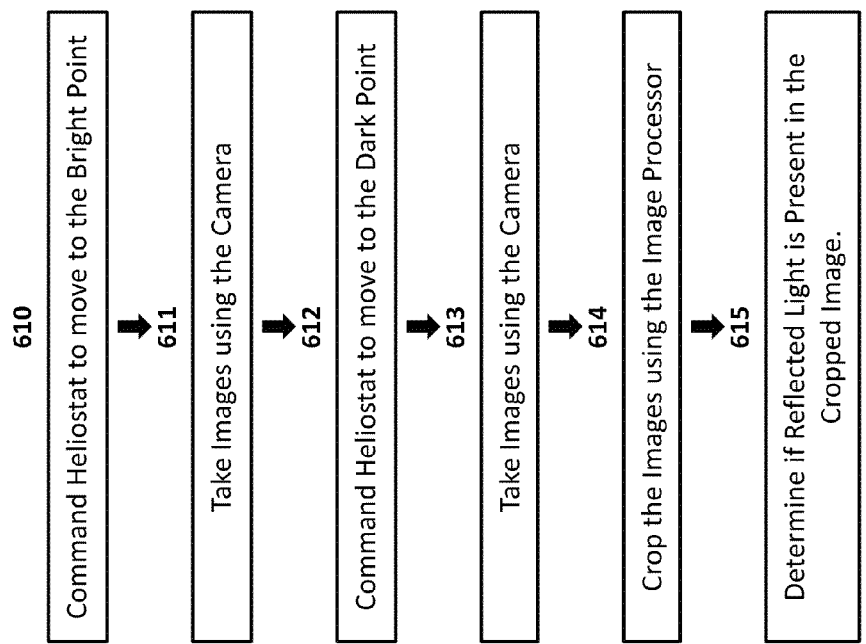
FIG. 6 is a flowchart detailing an embodiment of the method by which a spot-check test is performed on an individual heliostat.

FIG. 6 displays a flowchart detailing the method of executing an individual spot-check test, which encompasses step a) of the monitoring phase (see FIG. 5). Each spot-check test may comprise the following steps:

a) Command the heliostat-under-test via motor inputs to move to the position that corresponds to the bright point (610).
b) Obtain a first sequence of real-time images of the light reflected from the heliostat using the camera (611).
c) Command the heliostat-under-test via motor inputs to move to the position that corresponds to the dark point (612).
d) Obtain, using the camera, a second sequence of real-time images of the light reflected from the heliostat using the camera (613).
e) Crop, using the image processor, both the first and second sequences of images to include only the portions of the image containing the heliostat (614).
f) Determine whether the reflected stationary light is present in the cropped image (615). This determination may be done by a number of methods, including feature recognition and "light flashing". Feature recognition involves synthesizing the sequence of images of the bright point into a single composite image using the image processor and then filtering the single image for transient contamination and noise. This filter may be, for example, a pixel-wise median filter. Next, the images of the dark point are synthesized into a single composite image using the same technique as with the images of the bright point. Finally, a feature recognition filter may be applied to both composite images to search for and identify a feature having the brightness and color of the expected reflected stationary light. This feature recognition filter may be, for example, a connected component labeling algorithm.

The method of "light flashing" involves flashing the stationary light on and off in coordination with the camera imager, such that images are taken of the heliostat region in the presence, and in the absence, of the reflected light. Each stationary light may be flashed at the same frequency, at different frequencies, or at the same frequency at a phase offset from one another. For each sequence of images, the image processor may then be used to interlace an image of the heliostat region with the light switched "off" with an image of the heliostat with the light switched "on" and compare the images to identify a feature having the brightness and color of the expected stationary light. The means of comparing the images may be, for example, a method of subtracting features of one set of images from the other.

g) Determine the outcome of the test (616). The test may be determined to be successful if the light is visible in the sequenced images when the heliostat is at the bright point and is not visible when the heliostat is at the dark point. Alternatively, the pass or failure condition may be defined by the number of bright points which do not produce a reflection of viewable light on the camera and/or the number of dark points that do produce a reflection of viewable light. As a first example, the heliostat may be determined to have failed the spot-check test if it reflects viewable light to the camera from a number of bright points below a predetermined threshold, and to have passed if the converse is true. As a second example, the heliostat may be determined to have failed the spot-check test if the number of dark points that fail to produce a reflection meets, or exceeds, a predetermined threshold, and to have passed if the converse is true. The result of the spot-check test may be saved to a central database immediately, or the test may be repeated at least once more for confirmation. If the test is repeated, it may be repeated with a higher fidelity, for example by taking a greater number of images of the heliostat bright and dark points or by taking higher quality images. The test may also be repeated upon establishing a greater distance between the bright and dark points; this method decreases the resolution of the test but reduces its sensitivity to small perturbations of the heliostat, which may occur during vibration events such as those caused by high speed winds.

If a heliostat fails the spot-check test, it may be flagged for additional investigation, repair, replacement, or recalibration. The outcome of the test may be saved to the database along with additional corresponding diagnostic information, such as metadata concerning the state of the heliostat throughout the test, environmental data such as wind speed or ambient temperature, and the results of any subsequent or previous tests in which reflected light was identified in an image of the same heliostat. If it is found that a heliostat fails the test under certain conditions and passes under others, a higher fidelity test may be repeated. A high fidelity spot-check test may comprise the selection of multiple bright and dark points, or the sampling of multiple camera images of each point.

A benefit of the failure detection method according to the present invention is that spot-check tests may be performed rapidly without interfering with plant power production. Spot-check tests may be made during the day by reflecting the sun onto the camera, or during the night by reflecting flux from the stationary lights. Spot-check tests may be performed by reflecting a single stationary light from a single heliostat onto a single camera, or by reflecting a plurality of lights from a plurality of heliostats onto a plurality of cameras, or from a plurality of heliostats onto the same camera. If a plurality of heliostats is commanded to reflect light from a plurality of lights onto a single camera simultaneously, the images taken by the camera may be separated into regions, wherein each region contains the reflected light from a single heliostat. In this way, light reflected from heliostats in non-interfering regions of the image are more easily discernible from each other.

For plants comprising a plurality of heliostats, parallel testing may reduce the time it takes to spot-check an entire field. This may be done by optimally scheduling subsequent spot-check tests on heliostats in different regions of the field. In a first embodiment, scheduling of heliostat spot-check tests may be performed deterministically. Deterministic scheduling involves running spot-check tests of fixed duration. In this embodiment, non-interfering sets comprising a plurality of heliostats may be selected for failure mode detection testing such that each set may be actuated to reflect light onto a single camera simultaneously. For a given amount of time, each heliostat in the non-interfering set may undergo a spot-check test; when the given time has elapsed, the set-under-test may be replaced by a subsequent non-interfering set. This process may be repeated until all heliostats requiring a functional check have been tested. Additionally, heliostats may be queued for spot-check tests while other tests are taking place. Deterministic scheduling is advantageous because it allows for the total duration of failure-mode detection to be known prior to testing, and because querying the cameras for images may be streamlined by consolidating requests for heliostats undergoing simultaneous spot-checks.

In a second embodiment, scheduling of heliostat spot-check tests may be performed adaptively. Adaptive scheduling involves running spot-check tests of varying duration. In this embodiment, heliostats may be selected for failure mode detection testing based on an objective function, subject to the constraint that no two simultaneous spot checks may interfere with one another. The objective function may prioritize, for example, heliostats which have a higher assumed likelihood of failure. Spot-check tests are performed on subsequent sets of heliostats until they are completed, regardless of duration. The data collection rate may be dynamically controlled based on other plant activities or constraints. For example, if heliostat motion results in higher-than-desired power consumption due to motor actuation, the number of heliostats that are scheduled for spot-check tests during a given time may be throttled to a lower amount. As with deterministic scheduling, heliostats may be queued for spot-check tests while other tests are taking place. Adaptive scheduling is advantageous because spot-check throughput may be made consistent regardless of the duration allotted for test execution, and because heliostats with a higher chance of repair may be tested for functionality first, reducing the average mean-time-to-repair (MTTR).

The results of completed spot-check tests may be saved to a database upon completion. The results may comprise, for example, a Boolean value, such as Pass or Fail, or a file containing the set of camera images obtained during the test. The image processor may further comprise a reporting software application. The reporting software application may execute to produce a report from a set of spot-check tests. The report may include a list of all failed or successful spot-check tests, a list of heliostats, stationary lights, or cameras which are expected to have failed, a recommended priority of heliostats to be repaired, a depiction of the location of failed heliostats, or a suggested route for maintenance personnel to access each failed heliostat in a minimal amount of time. Reports may be generated in real time, at a regular interval, or upon request by plant personnel. Reports themselves may also be saved to the database upon creation.

Results from completed spot-check tests, once saved to the database, may be reported to an automated software application or to users for analysis, at which point the method of failure detection may be modified to improve plant performance. Users may comprise, for instance, plant maintenance personnel. For example, parasitic electrical losses associated with actuating heliostats and control system hardware during non-power producing hours may be weighed against the benefits of improved availability to determine an optimal rate of scheduling spot-check tests. Spot-check tests may also be prioritized for heliostats that may be more susceptible to failure; these heliostats may be located in a particular location, have demonstrated poor performance in the past, or may be associated with a particular subgroup. Said subgroups may include, for example, heliostats from the same manufacturer or heliostats having the same date of installation. Finally, metrics for determining whether a failed heliostat should be repaired or replaced may be refined based on manual inspection. These and other adjustments to the spot-check tests can be made automatically by said automatic software application or manually by said users. The automatic software application may further be configured to conduct additional tests and gather diagnostics pending the results of the spot-check tests.

Various combinations and/or sub-combinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further it is intended that the scope of the present invention herein disclosed by way of examples should not be limited by the particular disclosed embodiments described above.

I claim:

1. A method for detecting heliostat failures, the method comprising a commissioning phase followed by a monitoring phase, wherein the commissioning phase comprises the steps of:
   (a) Calibrating a heliostat;
   (b) Selecting said heliostat, a camera, and a stationary light and associating them as a heliostat-camera-light triplet;
   (c) Determining bright and dark points for said heliostat-camera-light triplet; and
   (d) Storing the bright and dark points for said heliostat-camera-light triplet in a database;

and wherein the monitoring phase comprises the steps of:
   (a) Selecting a heliostat;
   (b) Performing a spot-check test on said heliostat;
   (c) Storing the results of said spot-check test in a database;
   (d) Processing the results of said spot-check test;
   (e) Delivering notification of the results of said spot-check test; and
   (f) Adjusting the frequency and sample population of future spot-check tests based on said results.

2. The method of detecting heliostat failures according to claim 1, wherein the commissioning phase comprises the additional step of administering a pointing test to said heliostat, and wherein said additional step occurs after step (a) and before step (b).

3. The method of detecting heliostat failures according to claim 2, wherein the commissioning phase comprises the additional step of simulating the expected performance of said heliostat, wherein said additional step occurs after the step of claim 2 and before step (b).

4. The method of detecting heliostat failures according to claim 1, wherein said spot-check test comprises the steps of:
   (a) Commanding said heliostat to move to the position of a bright point using a control system;
   (b) Taking, with the camera, a first sequence of images of the heliostat;
   (c) Commanding said heliostat to move to the position of a dark point using a control system;
   (d) Taking, with the camera, a second sequence of images of the heliostat;
   (e) Cropping, using an image processor, said first and second sequences of images to only include regions where said heliostat is present; and
   (f) Determining if reflected light from the heliostat is present in the first and second sequences of images.

5. The method of claim 4, wherein determining if reflected light from the heliostat is present in the cropped image is achieved by a feature recognition algorithm.

6. The method of claim 1, wherein the bright points comprise heliostat motor positions that result in a reflection of said stationary light from said heliostat onto said camera.

7. The method of claim 1, wherein the dark points comprise heliostat motor positions that do not result in a reflection of said stationary light from said heliostat onto said camera.

8. The method of claim 1, wherein the bright and dark points are separated from each other in an axial direction by less than 1 milliradian.

9. The method of claim 1, wherein said heliostat is determined to have experienced a failure mode if it fails said spot-check test.

10. The method of claim 1, wherein the method is performed at night-time.

11. The method of claim 1, wherein the results of said spot-check test are delivered to a user.

12. The method of claim 1, wherein the results of said spot-check test are delivered to an automated software application.

* * * * *